US00PP27498P2

(12) United States Plant Patent
Hansen

(10) Patent No.: US PP27,498 P2
(45) Date of Patent: Dec. 20, 2016

(54) ***MONARDA* PLANT NAMED 'GRAPE GUMBALL'**

(50) Latin Name: *Monarda didyma*
Varietal Denomination: Grape Gumball

(71) Applicant: Hans A. Hansen, Zeeland, MI (US)

(72) Inventor: Hans A. Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 10 days.

(21) Appl. No.: 14/545,862

(22) Filed: Jun. 30, 2015

(51) Int. Cl.
*A01H 5/02* (2006.01)

(52) U.S. Cl.
USPC ..... Plt./455

(58) Field of Classification Search
USPC ..... Plt./455
See application file for complete search history.

*Primary Examiner* — Susan McCormick Ewoldt

(57) ABSTRACT

The new and distinct plant of ornamental bee balm named *Monarda didyma* 'Grape Gumball' has rapid-growing, compact, branching stems, dark green foliage, numerous magenta flowers with dark purplish tinted stems. Foliage has good resistance to powdery mildew.

1 Drawing Sheet

BOTANICAL DESIGNATION AND CULTIVAR DENOMINATION

Botanical classification: *Monarda didyma.*
Variety denomination: 'Grape Gumball'.

CROSS REFERENCE TO RELATED PLANTS

FEDERAL SPONSORSHIP AND FUNDING

This plant invention was developed without federally sponsored research or development funding.

BACKGROUND OF THE INVENTION

The present invention relates to the new and distinct plant cultivar botanically known as *Monarda didyma* 'Grape Gumball', and hereinafter also referred to solely as the cultivar 'Grape Gumball' or the "new plant". The new plant was the subject of an open pollination in the summer of 2010 by the inventor at a wholesale perennial nursery in Zeeland, Mich., USA. The seed or female parent was the unreleased proprietary hybrid HK9-43-126 (not patented) and the pollen or male parent was unknown but may have been any one of several plants and seedlings in the isolated breeding area since the pollen is efficiently spread long distances by insects. The individual plant was subjected during the summer of 2012 to initial evaluation in outdoor trial plots belonging to the same nursery in Zeeland, Mich. and was later given the breeder identification number of H10-13-3. Final evaluation was performed in the summer of 2013 wherein a single selected seedling was separated for eventual introduction.

*Monarda* 'Grape Gumball' has been asexually propagated by stem cuttings at the same nursery in the greenhouses in Zeeland, Mich., and the subsequent asexually propagated plants found to be stable and identical to the original selection.

BRIEF SUMMARY OF THE PLANT

*Monarda* 'Grape Gumball' is unique from its parent and all other bee balm plants known to the inventor. The nearest comparison varieties are 'Purple Rooster' (not patented), 'Leading Lady Plum' U.S. Plant Pat. No. 26,447 and 'ACrade' (U.S. Plant Pat. No. 19,580) in plant habit. Compared to 'Purple Rooster', the new plant has larger flowers that are more magenta and less purple, and 'Purple Rooster' is significantly taller. 'Grape Gumball' is taller than 'ACrade' and the female parent and also has a more reddish coloring to the flowers than 'ACrade' or the female parent. Compared to 'Leading Lady Lilac' U.S. Plant Pat. No. 26,431 and 'Leading Lady Plum' U.S. Plant Pat. No. 26,447, the new plant is more reddish in flower color and does not have the darker purple spotting of both the former two cultivars.

The table below shows a more detailed comparison of these and other cultivars in terms of flower color and height.

TABLE 1

| CULT1VAR | FLOWER COLOR | HEIGHT |
|---|---|---|
| 'Achall' U.S. Plant Pat. No. 19582 | deep red-purple | 45 cm |
| 'Arcade' U.S. Plant Pat. No. 19580 | purple violet | 40 cm |
| 'Coral Reef' U.S. Plant Pat. No. 16741 | coral pink | 125 cm |
| 'Fire Marshall' U.S. Plant Pat. No. 23286 | deep red | 50 cm |
| 'Fireball' U.S. Plant Pat. No. 14235 | red-purple | 60 cm |
| 'Grape Gumball' | magenta | 60 cm |
| 'Leading Lady Lilac' U.S. Plant Pat. No. 26431 | light lilac purple with dark spots | 32 cm |
| 'Leading Lady U.S. Plant Pat. No. 26447 | magenta purple with dark spots | 34 cm |
| 'MCmum' U.S. Plant Pat. No. 22136 | pink | 60 cm |
| 'Mondid 0803' U.S. Plant Pat. No. 17513 | red-purple | 40 cm |
| 'Pardon My Pink' U.S. Plant Pat. No. 24244 | fuchsia-pink | 28 cm |
| 'Pardon My Purple' U.S. Plant Pat. No. 22170 | dark fuchsia | 30 cm |
| 'Petite Delight' U.S. Plant Pat. No. 10784 | light pink-purple | 30 cm |
| 'Petite Wonder' U.S. Plant Pat. No. 13149 | light pink | 25 cm |
| 'Pink Lace' U.S. Plant Pat. No. 18367 | red-purple | 45 cm |

TABLE 1-continued

| CULT1VAR | FLOWER COLOR | HEIGHT |
|---|---|---|
| 'Pink Supreme' U.S. Plant Pat. No. 14204 | deep pink | 60 cm |
| 'Purple Rooster' | royal purple | 90 cm |
| 'Sugar Lace' U.S. Plant Pat. No. 22918 | red-purple | 45 cm |

The following are traits of *Monarda didyma* 'Grape Gumball' that in combination distinguish it from all other bee balm known to the inventor;

1. Moderate growth rate, intermediate height, compact, very tight clumping habit.
2. Dark-green, powdery mildew resistant foliage.
3. Dark purplish tinted stems.
4. Magenta flowers for a long period in summer.

BRIEF DESCRIPTION OF THE DRAWINGS

The photographs of the new plant demonstrate the unique traits of 'Grape Gumball' and the overall appearance of the plant at three-years-old in the full sun trial garden of a nursery in Zeeland, Mich. The colors are as accurate as reasonably possible with current color reproduction technology. Deviation in ambient light spectrum, source and direction may cause the appearance of minor variation in color.

DETAILED BOTANICAL DESCRIPTION

Figure 1:
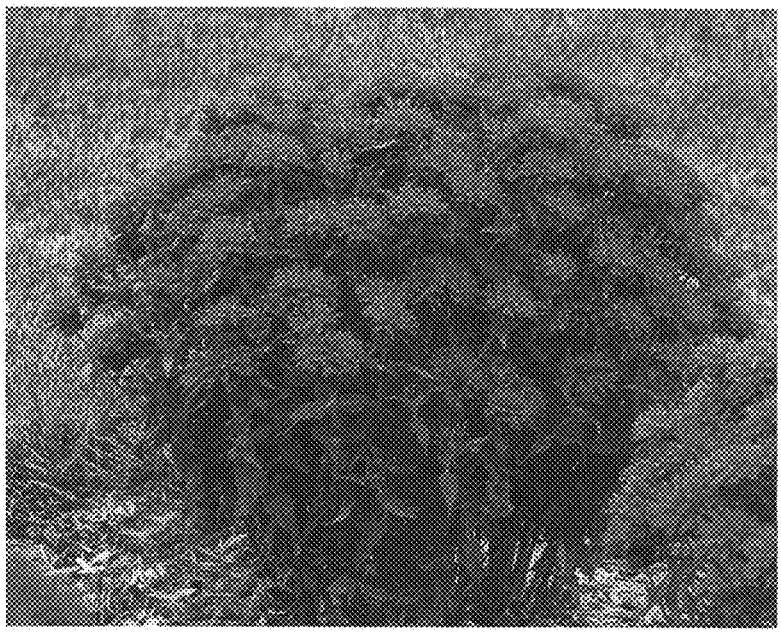
FIG. 1 shows the new plant in flower.
Figure 2:
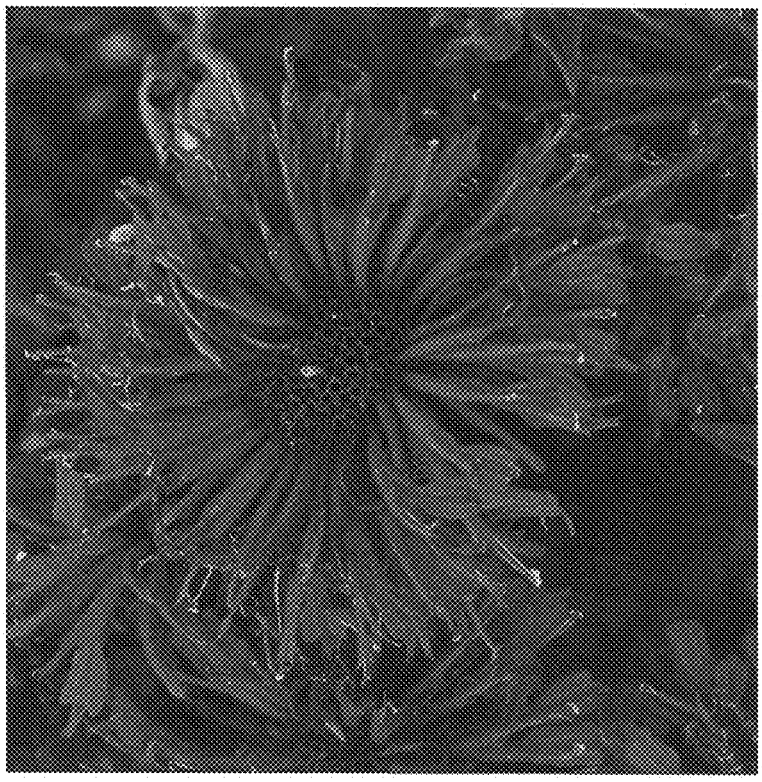
FIG. 2 shows a close-up of the flowers.

The following descriptions and color references are based on the 2001 edition of The Royal Horticultural Society Colour Chart except where common dictionary terms are used. *Monarda didyma* 'Grape Gumball' has not been observed under all possible environments. The phenotype may vary slightly with different growing environments such as temperature, light, fertility, soil pH, moisture and maturity levels, but without any change in the genotype. The following observations and size descriptions are based on two-year old garden-grown plants in full sun at a nursery in Zeeland, Mich. with minimal supplemental fertilizer and water as needed but without plant growth regulators or pinching.

Botanical classification: *Monarda didyma.*

Parentage:

*Female (seed) parent.*—Is *Monarda didyma* HK9-43-126 (not patented).

*Male (pollen) parent.*—Is unknown.

Plant habit: Hardy, herbaceous, tightly compact perennial, producing several stems, spreading by short rhizomes; about 35.0 cm tall at flowering and about 50.0 cm wide; flowering begins mid-summer in Michigan and continues for about 5 to 7 weeks.

Propagation: Stem cuttings.

Time to produce finished crop in 3.8 liter pots: About 7 to 9 weeks; moderately fast rate of growth.

Root: Fine, fibrous and freely branching; color creamy white to tan depending on soil type.

Leaves: Simple, lanceolate, opposite, serrated, slightly puberulent above and puberulent below; surfaces lustrous above, matte below; acute apex, ovate to rounded base; average about 5.5 cm long by about 2.5 cm wide.

*Leaf color.*—Young leaves between RHS N144C and RHS 143C above and between RHS 143C and RHS 138B below; older leaves nearest RHS 136A above and between RHS 135A and RHS 136B below.

Foliage fragrance: Pleasantly lemony.

Veins: Pinnate; pubescent below with minutely puberulent above, slightly sunken above and raised below.

*Vein color.*—Adaxial midrib between RHS 138C and RHS 139D with tinting of between RHS N187C and lighter than RHS N77D toward the distal end and in areas of high light exposure, center portion of lateral veins nearest RHS 138C above with distal vein portion nearest RHS 136A; abaxial midrib and center portion of lateral veins between RHS 138D and RHS 138C with distal portion of lateral veins between RHS 135A and RHS 136B below.

Petiole: Pubescent, slightly concaved above; average about 3.0 mm long and 2.0 mm across.

*Petiole color.*—Between RHS 137B and RHS 138B above and below with slight tinting of nearest RHS N186C where exposed to intense direct sunlight.

Stems: Squared, puberulent, densely pubescent at nodes; 4.0 to 6.0 mm across at base, average about 5.0 mm across; branched with four to six branches.

*Nodes.*—8 to 10 per stem; average internode length about 4.0 cm, closer at base; node color same as surrounding stem with some tinting of nearest RHS N186 C in regions of high light.

*Stem color.*—Between RHS 137C and RHS 137D with stippling of nearest RHS 187B becoming concentrated in upper portion, especially at nodes.

Flowers: Single labiate flowers arranged in terminal globular head to about 8.0 cm across and 4.8 cm tall opening from the center and progressing outwardly and down; individually persisting about 5 days in Michigan; numerous, about 280 flowers per head; self-cleaning.

Flower fragrance: Moderately spicy.

Buds one to two days prior to opening: Narrowly oblanceolate, distinctly curved downward; about 2.3 cm long and 3.0 mm diameter.

*Bud color one to two days prior to opening.*—Nearest RHS 72A in the apical region with the center portion between RHS 64B and RHS 71C with a lighter base inside corolla of white, lighter than RHS N155D or RHS 155D.

Petals: Labiate; lower curved downward and upper nearly straight; split in two in the distal 1.0 cm with upper lip fused into a hood about 2.9 cm long and 2.5 mm diameter; lower lip about 3.1 cm long comprising three lobes including two side lobes about 1.0 mm long with rounded apex and center lobe about 4.0 to 5.0 mm long split in the distal 1.0 mm with acute apex, curled up almost 90 degrees; both side lobes glandular and pubescent outer surfaces with fine hairs the same color as petals; both lobes glabrous on inner surfaces.

*Petal color.*—Color of all petals on both surfaces between RHS 64B and RHS 64C with basal 5.0 mm white, lighter than RHS 155D or RHS N155D.

Filaments: Two, about 2.8 cm long by about 0.7 mm diameter across at the widest point.

*Filament color.*—Lighter than RHS N155D in the middle portion and below developing slight distal tinting of lighter than RHS 77D.

Anther: Oblong elliptic, dorsifixed, longitudinal; about 2.5 mm long by about 1.0 mm across.

*Anther color.*—Nearest RHS 167C.

Pollen: Abundant, elliptic to globose, less than 0.1 mm; color nearest RHS 15D.

Pistil: One per flower.

Style: About 3.4 cm long by about 0.25 mm diameter; color nearest RHS N155C with tinting increasing at distal end to nearest RHS 70B.

Stigma: Split in two in the distal 2.0 mm, less than 0.25 mm in diameter; color nearest RHS 70B.

Ovary: 1.0 mm by 0.75 mm, between RHS 143D and RHS 144B.

Sepals: Five, entire, apiculate apex, base fused forming corolla about 9.0 mm long split in about the apical 2.0 mm, about 2.0 mm diameter at base and about 3.0 mm diameter at distal end; apex glandular and with minute hairs on outer surface, glabrous on inner surface.

*Sepal color*.—More green than RHS 186D and more purple than RHS 191B.

Peduncle: Pubescent, stiff, strong, branched, erect, squared to about 0.6 cm across at base and 37.0 cm long.

*Peduncle color*.—Between RHS 137C and RHS 137D with stippling of nearest RHS 187B becoming concentrated in upper portion, especially at nodes.

Bracts: Five to nine subtending flower head; acute to apiculate apex with base sessile and truncate; size decreasing distally, to about 1.5 cm long and 1.2 cm wide at base.

*Bract color*.—Lowest bracts same color as leaves, distally becoming more marginally pigmented to between RHS 187A and RHS N187A in both abaxial and adaxial surfaces; uppermost bracts between RHS 187B and RHS 189A; veining nearest RHS 187D both surfaces.

Fruit single nutlet: Elliptical, about 1.0 mm long and 0.7 mm wide; color nearest RHS 202A.

Hardiness: The new plant grows best with plenty of moisture and adequate drainage; hardy from at least from USDA zone 4 through 8.

Disease and pest resistance: Demonstrated powdery mildew resistance in side by side comparison at least equal that of 'ACrade' and better than 'AChall'.

I claim:

1. A new and distinct plant cultivar *Monarda didyma* 'Grape Gumball', as herein described and illustrated, resistant to powdery mildew and suitable for the garden landscape, or as a potted plant, patio, and for cut flower arrangements.

* * * * *